United States Patent
Mirar

(10) Patent No.: US 12,239,489 B2
(45) Date of Patent: Mar. 4, 2025

(54) METHODS AND SYSTEMS FOR VISUALIZING CARDIAC ELECTRICAL CONDUCTION

(71) Applicant: GE Precision Healthcare LLC, Wauwatosa, WI (US)

(72) Inventor: Hani Mirar, Oslo (NO)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 125 days.

(21) Appl. No.: 17/651,394

(22) Filed: Feb. 16, 2022

(65) Prior Publication Data
US 2023/0255598 A1 Aug. 17, 2023

(51) Int. Cl.
*A61B 8/08* (2006.01)
*A61B 8/00* (2006.01)
*G06T 7/00* (2017.01)

(52) U.S. Cl.
CPC ............ *A61B 8/485* (2013.01); *A61B 8/0883* (2013.01); *A61B 8/463* (2013.01); *A61B 8/5223* (2013.01); *G06T 7/0012* (2013.01); *G06T 2207/10132* (2013.01); *G06T 2207/20084* (2013.01); *G06T 2207/30048* (2013.01)

(58) Field of Classification Search
CPC ....... A61B 8/485; A61B 8/0883; A61B 8/463; A61B 8/5223; G06T 7/0012; G06T 2207/10132; G06T 2207/20084; G06T 2207/30048
See application file for complete search history.

(56) References Cited

U.S. PATENT DOCUMENTS

| | | | |
|---|---|---|---|
| 6,628,743 B1* | 9/2003 | Drummond | G16H 30/20 378/15 |
| 2007/0049824 A1* | 3/2007 | Konofagou | G01S 7/52087 600/437 |
| 2008/0285819 A1* | 11/2008 | Konofagou | A61B 8/485 382/128 |
| 2015/0289840 A1* | 10/2015 | Konofagou | A61B 8/485 600/438 |
| 2017/0319068 A1* | 11/2017 | Luther | A61B 5/0044 |
| 2020/0214662 A1* | 7/2020 | Konofagou | A61B 8/4416 |

OTHER PUBLICATIONS

Konofagou et al. Electromechanical Wave Imaging With Machine Learning for Automated Isochrone Generation. IEEE Trans Med Imaging. Sep. 2021;40(9):2258-2271. doi: 10.1109/TMI.2021.3074808. Epub Aug. 31, 2021. PMID: 33881993; PMCID: PMC8410624.*

(Continued)

*Primary Examiner* — Bo Joseph Peng
(74) *Attorney, Agent, or Firm* — McCoy Russell LLP

(57) ABSTRACT

Various methods and systems are provided for a medical imaging system. In one embodiment, a method comprises generating cardiac ultrasound images from ultrasound imaging data of a heart, generating a spatio-temporal map of electrical impulses in the heart based on contraction and elongation of cardiac muscles depicted in the cardiac ultrasound images, and outputting the spatio-temporal map of the electrical impulses in the heart to a display device. In this way, the spatio-temporal map of the electrical impulses in the heart may visually indicate an electrical conduction path through the heart.

20 Claims, 5 Drawing Sheets

(56) References Cited

OTHER PUBLICATIONS

Christoph et al., Inverse mechano-electrical reconstruction of cardiac excitation wave patterns from mechanical deformation using deep learning. Chaos Dec. 1, 2020; 30 (12): 123134. https://doi.org/10.1063/5.0023751.*

Konofagou et al. (Imaging the electromechanical activity of the heart in vivo, PNAS, May 24, 2011, vol. 108, No. 21, 8565-8570, https://doi.org/10.1073/pnas.1011688108.*

Tabassian et al., Machine learning of the spatio-temporal characteristics of echocardiographic deformation curves for infarct classification; Int J Cardiovasc Imaging (2017) 33:1159-1167.*

Smiseth, O. et al., "Myocardial strain imaging: how useful is it in clinical decision making?," European Heart Journal, vol. 37, No. 15, Apr. 14, 2016, Available Online Oct. 27, 2015, 14 pages.

* cited by examiner

METHODS AND SYSTEMS FOR VISUALIZING CARDIAC ELECTRICAL CONDUCTION

FIELD

Embodiments of the subject matter disclosed herein relate to ultrasound imaging.

BACKGROUND

An ultrasound imaging system typically includes an ultrasound probe that is applied to a patient's body and a workstation or device that is operably coupled to the probe. During a scan, the probe may be controlled by an operator of the system and is configured to transmit and receive ultrasound signals that are processed into an ultrasound image by the workstation or device. The workstation or device may show the ultrasound images as well as a plurality of user-selectable inputs through a display device. The operator or other user may interact with the workstation or device to analyze the images displayed on and/or select from the plurality of user-selectable inputs.

BRIEF DESCRIPTION

In one aspect, a method includes generating cardiac ultrasound images from ultrasound imaging data of a heart, generating a spatio-temporal map of electrical impulses in the heart based on contraction and elongation of cardiac muscles depicted in the cardiac ultrasound images, and outputting the spatio-temporal map of the electrical impulses in the heart to a display device.

The above advantages, other advantages, and features of the present description will be readily apparent from the following detailed description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings, in which.

DETAILED DESCRIPTION

Embodiments of the present disclosure will now be described, by way of example, with reference to the FIGS. 1-6, which relate to various embodiments for cardiac ultrasound imaging. In particular, systems and methods are provided for visualizing an electrical conduction pathway through a heart of a patient. The contraction and relaxation of cardiac muscles results from muscle depolarization and repolarization, which is triggered by electrical impulses. The contraction and relaxation of the cardiac muscles results in longitudinal, circumferential, and radial strain values, which may be calculated via a strain tool used in cardiac ultrasound imaging (e.g., speckle tracking echocardiography). Such strain values may provide information on regions of the heart with impaired cardiac muscle function. However, the strain values may be difficult for a user to interpret, particularly because the three strain values may be difficult to combine to assess the health of the muscle in a given area. For example, contraction may only be impaired in one direction (e.g., only one of the longitudinal, circumferential, and radial strain values may show impairment), and this impairment may be obscured by the continued contraction in the other two directions. As a result, areas of impaired muscle function may not be identified.

Figure 1:
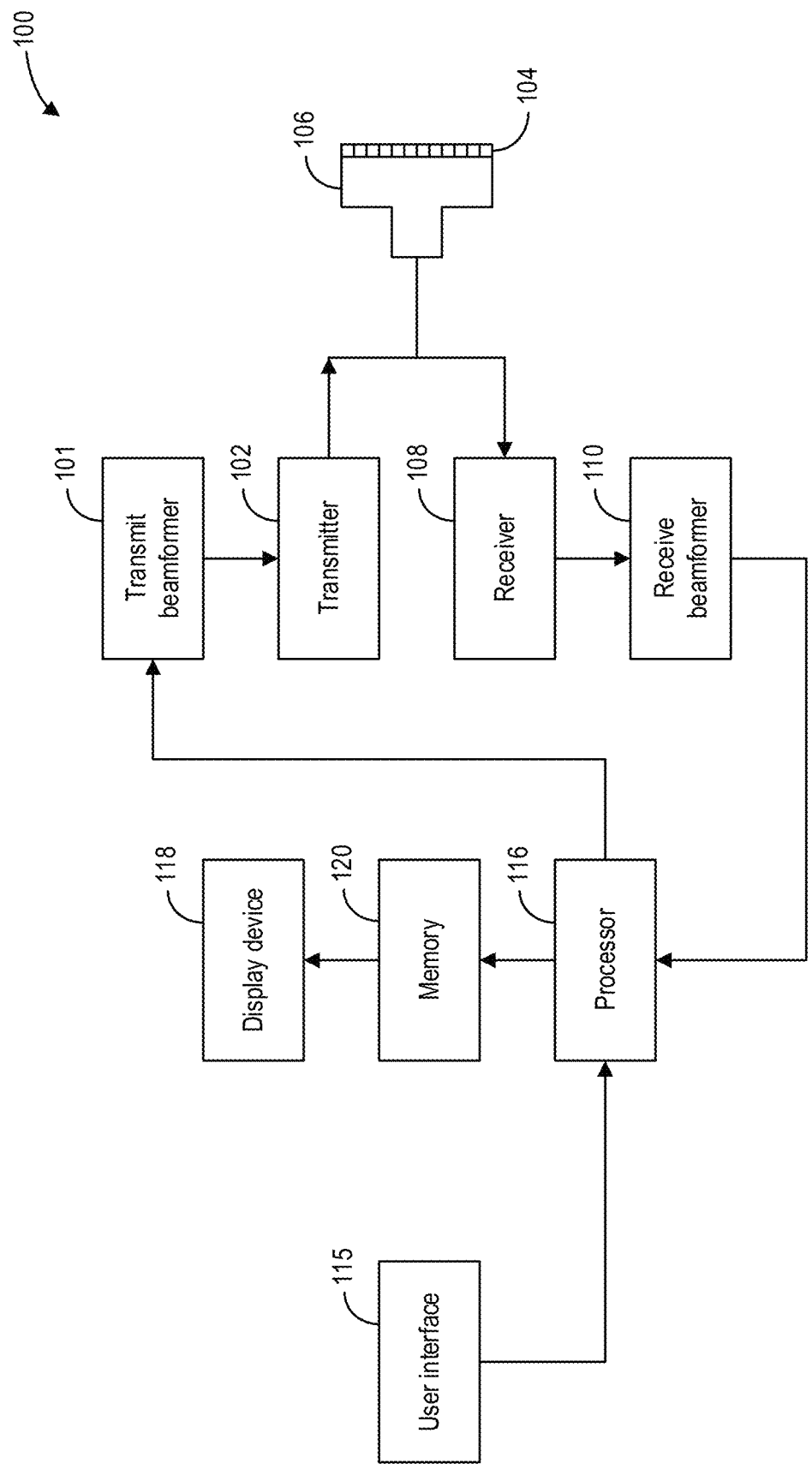
FIG. 1 shows a block schematic diagram of an ultrasound imaging system, according to an embodiment.
Figure 2:
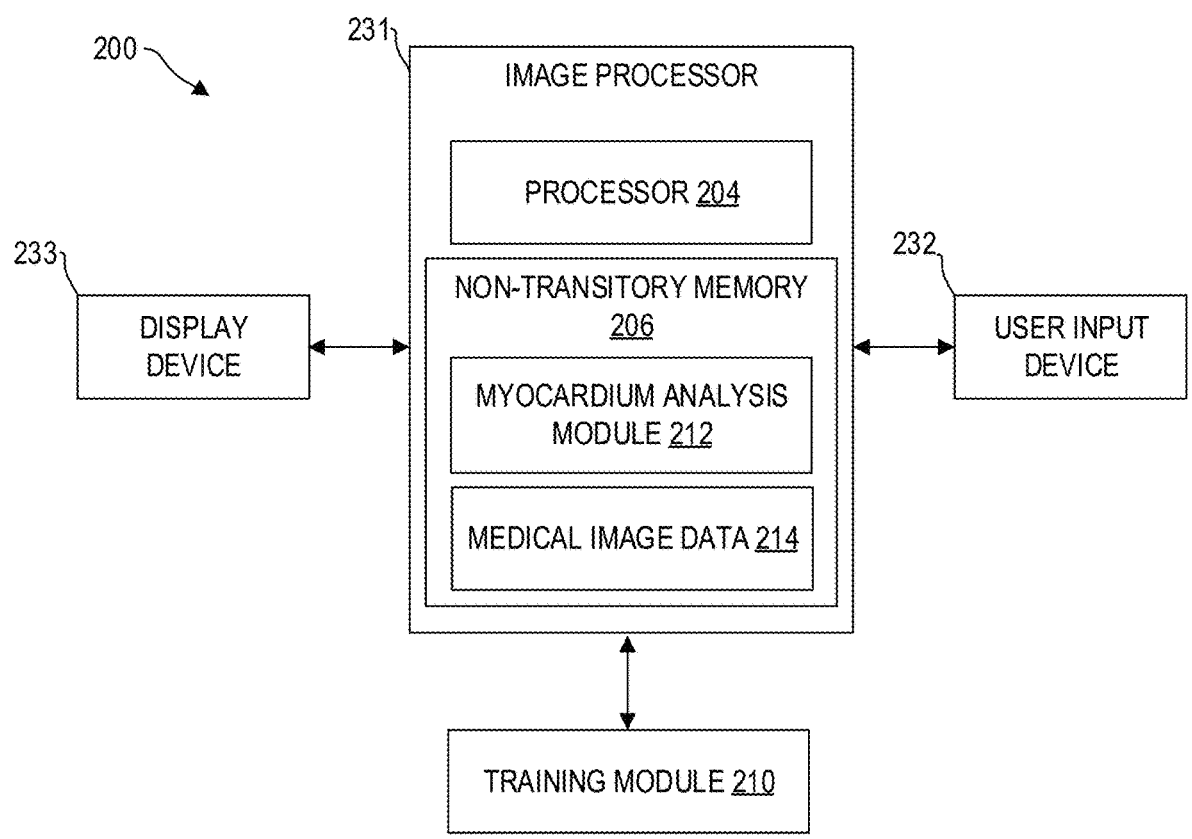
FIG. 2 is a schematic diagram illustrating an image processing system for segmenting myocardium in ultrasound images, according to embodiment.
Figure 4:
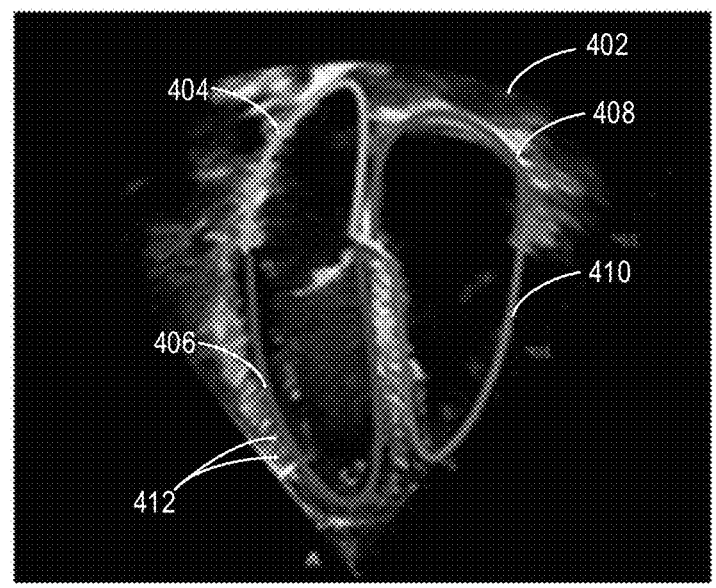
FIG. 4 shows an example myocardium segmentation, according to an embodiment.
Figure 5:
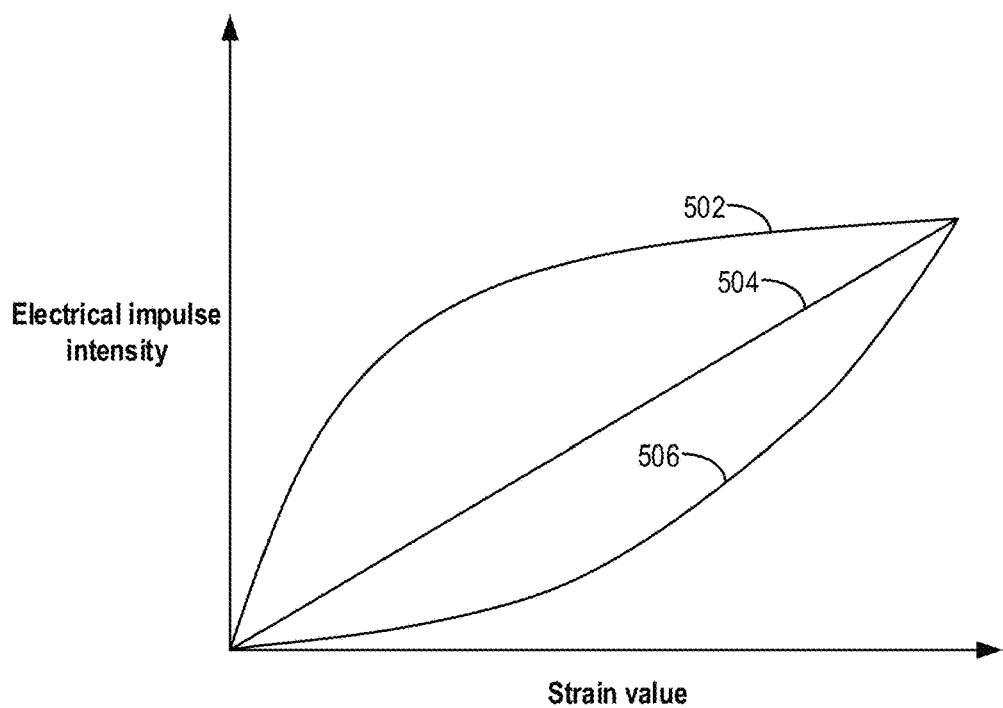
FIG. 5 is a graph showing example relationships between strain values and electrical impulse intensity.
Figure 6:
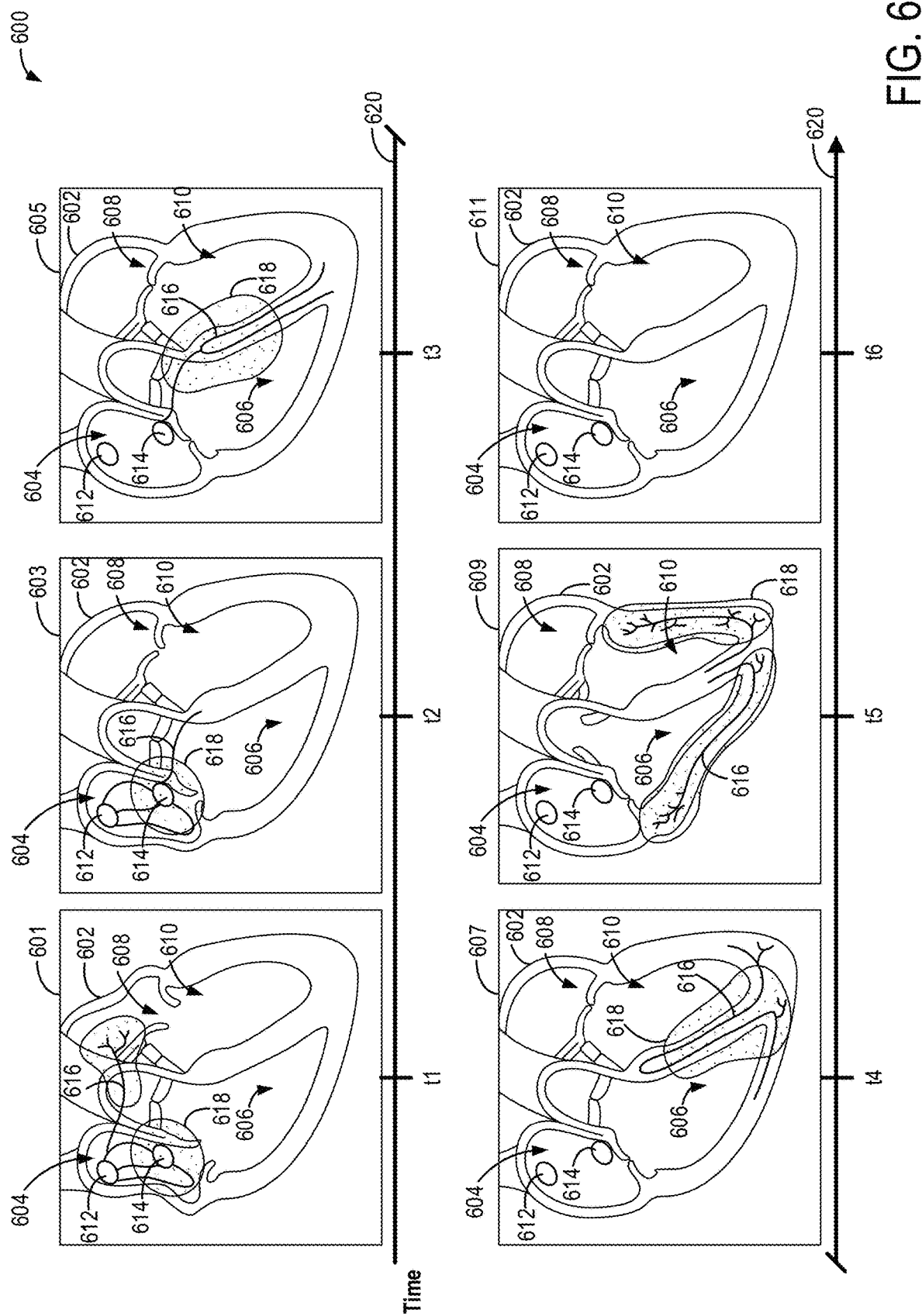
FIG. 6 shows an example cardiac electrical conduction path display output.

Thus, according to embodiments described herein, images of the heart may be acquired by an ultrasound imaging system, such as the ultrasound imaging system shown in FIG. 1. An example image processing system that may be used to segment cardiac muscle (e.g., myocardium) is shown in FIG. 2. The image processing system may employ image processing and deep learning algorithms to segment the myocardium within the ultrasound images, an example of which is shown in FIG. 4. The segmented ultrasound image may be further analyzed via speckle tracking echocardiography to determine contraction of the myocardium over time. Because myocardial contraction is caused by the passage of electrical impulses in the heart, strain values determined from the speckle tracking echocardiography may be used to generate a spatio-temporal map showing the passage of the electrical impulses through the heart, such as according to the method of FIG. 3. Example relationships between the strain values and an intensity of the electrical impulse is shown in FIG. 5. In some embodiments, the image processing system may also employ deep learning algorithms to directly compute the electrical conduction path from the ultrasound images without first computing the strain values via speckle tracking echocardiography. An example display output showing the spatio-temporal map of the passage of the electrical impulses through the heart, also referred to herein as a cardiac electrical conduction pathway, is shown in FIG. 6.

Advantages that may be realized in the practice of some embodiments of the described systems and techniques are that areas of impaired muscle function may be more easily identified. For example, generating a visualization of the cardiac electrical conduction pathway may show areas of impaired cardiac muscle function, as the electrical impulse does not travel through infarcted muscle. As such, the visualization of the cardiac electrical conduction pathway summarizes strain value quantities in all directions at once in a simple and intuitive way that does not rely on additional user interpretation. In this way, areas of impaired cardiac function may be more easily identified, resulting in more accurate and timely diagnoses.

Although the systems and methods described below for evaluating medical images are discussed with reference to an ultrasound imaging system, it may be noted that the methods described herein may be applied to a plurality of imaging systems. As the processes described herein may be applied to pre-processed imaging data and/or to processed images, the term "image" is generally used throughout the disclosure to denote both pre-processed and partially-processed image data (e.g., pre-beamformed radio frequency or in-phase/quadrature data, pre-scan converted radio frequency data) as well as fully processed images (e.g., scan converted and filtered images ready for display).

Referring to FIG. 1, a schematic diagram of an ultrasound imaging system 100 in accordance with an embodiment of the disclosure is shown. However, it may be understood that embodiments set forth herein may be implemented using other types of medical imaging modalities (e.g., magnetic resonance imaging, computed tomography, positron emission tomography, and so on). The ultrasound imaging system 100 includes a transmit beamformer 101 and a transmitter 102 that drives elements (e.g., transducer elements) 104 within a transducer array, herein referred to as a probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. The transducer elements 104 may be comprised of a piezoelectric material. When a voltage is applied to the piezoelectric material, the piezoelectric material physically expands and contracts, emitting an ultrasonic spherical wave. In this way, the transducer elements 104 may convert electronic transmit signals into acoustic transmit beams.

After the transducer elements 104 of the probe 106 emit pulsed ultrasonic signals into the body (of a patient), the pulsed ultrasonic signals are back-scattered from structures within an interior of the body, like blood cells and muscular tissue, to produce echoes that return to the elements 104. The echoes are converted into electrical signals, or ultrasound data, by the elements 104, and the electrical signals are received by a receiver 108. The electrical signals representing the received echoes are passed through a receive beamformer 110 that performs beamforming and outputs ultrasound data, which may be in the form of a radiofrequency (RF) signal. Additionally, the transducer elements 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be positioned within the probe 106. The terms "scan" or "scanning" may also be used in this disclosure to refer to acquiring data through the process of transmitting and receiving ultrasonic signals. The term "data" may be used in this disclosure to refer to one or more datasets acquired with an ultrasound imaging system. In one embodiment, data acquired via the ultrasound imaging system 100 may be processed via an imaging processing system, as will be elaborated below with respect to FIG. 2.

A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of a rotary element, a mouse, a keyboard, a trackball, hard keys linked to specific actions, soft keys that may be configured to control different functions, and a graphical user interface displayed on a display device 118. In some embodiments, the display device 118 may include a touch-sensitive display, and thus the display device 118 may be included in the user interface 115.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. As used herein, the term "electronic communication" may be defined to include both wired and wireless communications. The processor 116 may control the probe 106 to acquire data according to instructions stored on a memory of the processor and/or a memory 120. As one example, the processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processing unit (CPU), according to an embodiment. According to other embodiments, the processor 116 may include other electronic components capable of carrying out processing functions, such as a digital signal processor, a field-programmable gate array (FPGA), or a graphics board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphics board. According to another embodiment, the processor 116 may also include a complex demodulator (not shown) that demodulates RF data and generates raw data. In another embodiment, the demodulation may be carried out earlier in the processing chain.

The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay (e.g., substantially at the time of occurrence). For example, an embodiment may acquire images at a real-time rate of 7-20 frames/sec. The ultrasound imaging system 100 may acquire two-dimensional (2D) data of one or more planes at a significantly faster rate. However, it should be understood that the real-time frame-rate may be dependent on a length (e.g., duration) of time that it takes to acquire and/or process each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec.

In some embodiments, the data may be stored temporarily in a buffer (not shown) during a scanning session and processed in less than real-time in a live or off-line operation. Some embodiments of the disclosure may include multiple processors (not shown) to handle the processing tasks that are handled by the processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hertz (Hz) to 30 Hz (e.g., 10 to 30 frames per second). Images generated from the data may be refreshed at a similar frame-rate on the display device 118. Other embodiments may acquire and display data at different rates. For example, some embodiments may acquire data at a frame-rate of less than 10 Hz or greater than 30 Hz depending on the size of the frame and the intended application. The memory 120 may store processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present disclosure, data may be processed in different mode-related modules by the processor 116 (e.g., B-mode, Color Doppler, M-mode, Color M-mode, spectral Doppler, elastography, tissue velocity imaging, strain, strain rate, and the like) to form 2D or three-dimensional (3D) images. When multiple images are obtained, the processor 116 may also be configured to stabilize or register the images. For example, one or more modules may generate B-mode, color Doppler, M-mode, color M-mode, color flow imaging, spectral Doppler, elastography, tissue velocity imaging (TVI), strain (e.g., speckle tracking echocardiography), strain rate, and the like, and combinations thereof. As one example, the one or more modules may process B-mode data, which may include 2D or 3D B-mode data, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image loop (e.g., cine loop) in real-time while a procedure (e.g., ultrasound imaging) is being performed on the patient. The video processor module may include a separate image memory, and the ultrasound images may be written to the image memory in order to be read and displayed by the display device 118.

Further, the components of the ultrasound imaging system 100 may be coupled to one another to form a single structure, may be separate but located within a common room, or may be remotely located with respect to one another. For example, one or more of the modules described herein may operate in a data server that has a distinct and remote location with respect to other components of the ultrasound imaging system 100, such as the probe 106 and the user interface 115. Optionally, the ultrasound imaging system 100 may be a unitary system that is capable of being moved (e.g., portably) from room to room. For example, the ultrasound imaging system 100 may include wheels or may be transported on a cart, or may comprise a handheld device.

For example, in various embodiments of the present disclosure, one or more components of the ultrasound imaging system 100 may be included in a portable, handheld ultrasound imaging device. For example, the display device 118 and the user interface 115 may be integrated into an exterior surface of the handheld ultrasound imaging device, which may further contain the processor 116 and the memory 120 therein. The probe 106 may comprise a handheld probe in electronic communication with the handheld ultrasound imaging device to collect raw ultrasound data. The transmit beamformer 101, the transmitter 102, the receiver 108, and the receive beamformer 110 may be included in the same or different portions of the ultrasound imaging system 100. For example, the transmit beamformer 101, the transmitter 102, the receiver 108, and the receive beamformer 110 may be included in the handheld ultrasound imaging device, the probe, and combinations thereof.

Referring now to FIG. 2, an example medical image processing system 200 is shown. In some embodiments, the medical image processing system 200 is incorporated into a medical imaging system, such as an ultrasound imaging system (e.g., the ultrasound imaging system 100 of FIG. 1), a magnetic resonance imaging (MRI) system, a computed tomography (CT) system, a single-photon emission computed tomography (SPECT) system, and the like. In some embodiments, at least a portion of the medical image processing system 200 is disposed at a device (e.g., an edge device or server) communicably coupled to the medical imaging system via wired and/or wireless connections. In some embodiments, the medical image processing system 200 is disposed at a separate device (e.g., a workstation) that can receive images from the medical imaging system or from a storage device that stores the images generated by the medical imaging system. The medical image processing system 200 may comprise an image processor 231, a user input device 232, and a display device 233. For example, the image processor 231 may be operatively/communicatively coupled to the user input device 232 and the display device 233.

The image processor 231 includes a processor 204 configured to execute machine readable instructions stored in a non-transitory memory 206. The processor 204 may be single core or multi-core, and the programs executed by the processor 204 may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration. In some embodiments, the processor 204 may include other electronic components capable of carrying out processing functions, such as a digital signal processor, a FPGA, or a graphics board. In some embodiments, the processor 204 may include multiple electronic components capable of carrying out processing functions. For example, the processor 204 may include two or more electronic components selected from a plurality of possible electronic components, including a central processor, a digital signal processor, a field-programmable gate array, and a graphics board. In still further embodiments, the processor 204 may be configured as a graphical processing unit (GPU), including parallel computing architecture and parallel processing capabilities.

In the embodiment shown in FIG. 2, the non-transitory memory 206 stores a myocardium analysis module 212 and medical image data 214. The myocardium analysis module 212 includes one or more algorithms, including machine learning models, to process input medical images from the medical image data 214. Specifically, the myocardium analysis module 212 may provide an artificial intelligence system for identifying cardiac muscle within the medical image data 214. For example, the myocardium analysis module 212 may include one or more deep learning networks comprising a plurality of weights and biases, activation functions, loss functions, gradient descent algorithms, and instructions for implementing the one or more deep learning networks to process the input medical images. Additionally or alternatively, the myocardium analysis module 212 may store instructions for implementing a neural network, such as a convolutional neural network, for identifying cardiac muscle captured in the medical image data 214. The myocardium analysis module 212 may include trained and/or untrained neural networks and may further include training routines, or parameters (e.g., weights and biases), associated with one or more neural network models stored therein. Additionally or alternatively, the myocardium analysis module 212 may include image recognition algorithms, shape or edge detection algorithms, and the like for identifying the cardiac muscle. In some embodiments, the myocardium analysis module 212 may evaluate the medical image data 214 as it is acquired in real-time. Additionally or alternatively, the myocardium analysis module 212 may evaluate the medical image data 214 offline, not in real-time.

In some embodiments, the myocardium analysis module 212 may further include trained and/or untrained neural networks for determining a cardiac electrical conduction pathway for the cardiac muscle identified in the medical image data 214. For example, the neural network may be trained using cardiac medical images (e.g., B -mode cardiac ultrasound images) and an associated electrical conduction pathway generated via speckle tracking echocardiography. After training, the electrical conduction pathway may be generated by the neural network directly from the cardiac medical images without first performing the speckle tracking echocardiography analysis.

The image processor 231 may be communicatively coupled to a training module 210, which includes instructions for training one or more of the machine learning models stored in the myocardium analysis module 212. The training module 210 may include instructions that, when executed by a processor, cause the processor to build a model (e.g., a mathematical model) based on sample data to make predictions or decisions regarding the electrical conduction pathway through the heart without the explicit programming of a conventional algorithm that does not utilize machine learning. In one example, the training module 210 includes instructions for receiving training data sets from the medical image data 214. The training data sets comprise sets of medical images (e.g., B-mode cardiac ultrasound images), associated ground truth labels/images, and associated model outputs (e.g., the electrical conduction pathway generated via speckle tracking echocardiography) for use in training one or more of the machine learning models stored in the myocardium analysis module 212. The training module 210 may receive medical images, associated ground truth labels/images, and associated model outputs for use in training the one or more machine learning models from sources other than the medical image data 214, such as other image processing systems, the cloud, etc. In some embodiments, one or more aspects of the training module 210 may include remotely-accessible networked storage devices configured in a cloud computing configuration. Further, in some embodiments, the training module 210 is included in the non-transitory memory 206. Additionally or alternatively, in some embodiments, the training module 210 may be used to generate the myocardium analysis module 212 offline and remote from the medical image processing system 200. In such embodiments, the training module 210 may not be included in the medical image processing system 200 but may generate data stored in the medical image processing system 200. For example, the myocardium analysis module 212 may be pre-trained with the training module 210 at a place of manufacture.

The non-transitory memory 206 further stores the medical image data 214. The medical image data 214 includes, for example, functional and/or anatomical images captured by an imaging modality, such as ultrasound imaging systems, MRI systems, CT systems, and so forth. As one example, the medical image data 214 may include ultrasound images, such as cardiac ultrasound images. Further, the medical image data 214 may include one or more of 2D images, 3D images, static single frame images, and multi-frame cine-loops (e.g., movies).

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices in a cloud computing configuration. As one example, the non-transitory memory 206 may be part of a picture archiving and communication system (PACS) that is configured to store patient medical histories, imaging data, test results, diagnosis information, management information, and/or scheduling information, for example.

The medical image processing system 200 may further include the user input device 232. The user input device 232 may comprise one or more of a touchscreen, a keyboard, a mouse, a trackpad, a motion sensing camera, or other device configured to enable a user to interact with and manipulate data stored within the image processor 231. As an example, the user input device 232 may enable a user to select images for analysis by the myocardium analysis module 212.

The display device 233 may include one or more display devices utilizing any type of display technology. In some embodiments, the display device 233 may comprise a computer monitor and may display unprocessed images, processed images, parametric maps, and/or exam reports. The display device 233 may be combined with the processor 204, the non-transitory memory 206, and/or the user input device 232 in a shared enclosure or may be a peripheral display device. The display device 233 may include a monitor, a touchscreen, a projector, or another type of display device, which may enable a user to view medical images and/or interact with various data stored in the non-transitory memory 206. In some embodiments, the display device 233 may be included in a smartphone, a tablet, a smartwatch, or the like.

It may be understood that the medical image processing system 200 shown in FIG. 2 is one non-limiting embodiment of an image processing system, and other imaging processing systems may include more, fewer, or different components without departing from the scope of this disclosure. Further, in some embodiments, at least portions of the medical image processing system 200 may be included in the ultrasound imaging system 100 of FIG. 1, or vice versa (e.g., at least portions of the ultrasound imaging system 100 may be included in the medical image processing system 200).

As used herein, the terms "system" and "module" may include a hardware and/or software system that operates to perform one or more functions. For example, a module or system may include or may be included in a computer processor, controller, or other logic-based device that performs operations based on instructions stored on a tangible and non-transitory computer readable storage medium, such as a computer memory.

Alternatively, a module or system may include a hard-wired device that performs operations based on hard-wired logic of the device. Various modules or systems shown in the attached figures may represent the hardware that operates based on software or hardwired instructions, the software that directs hardware to perform the operations, or a combination thereof.

"Systems" or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 3:
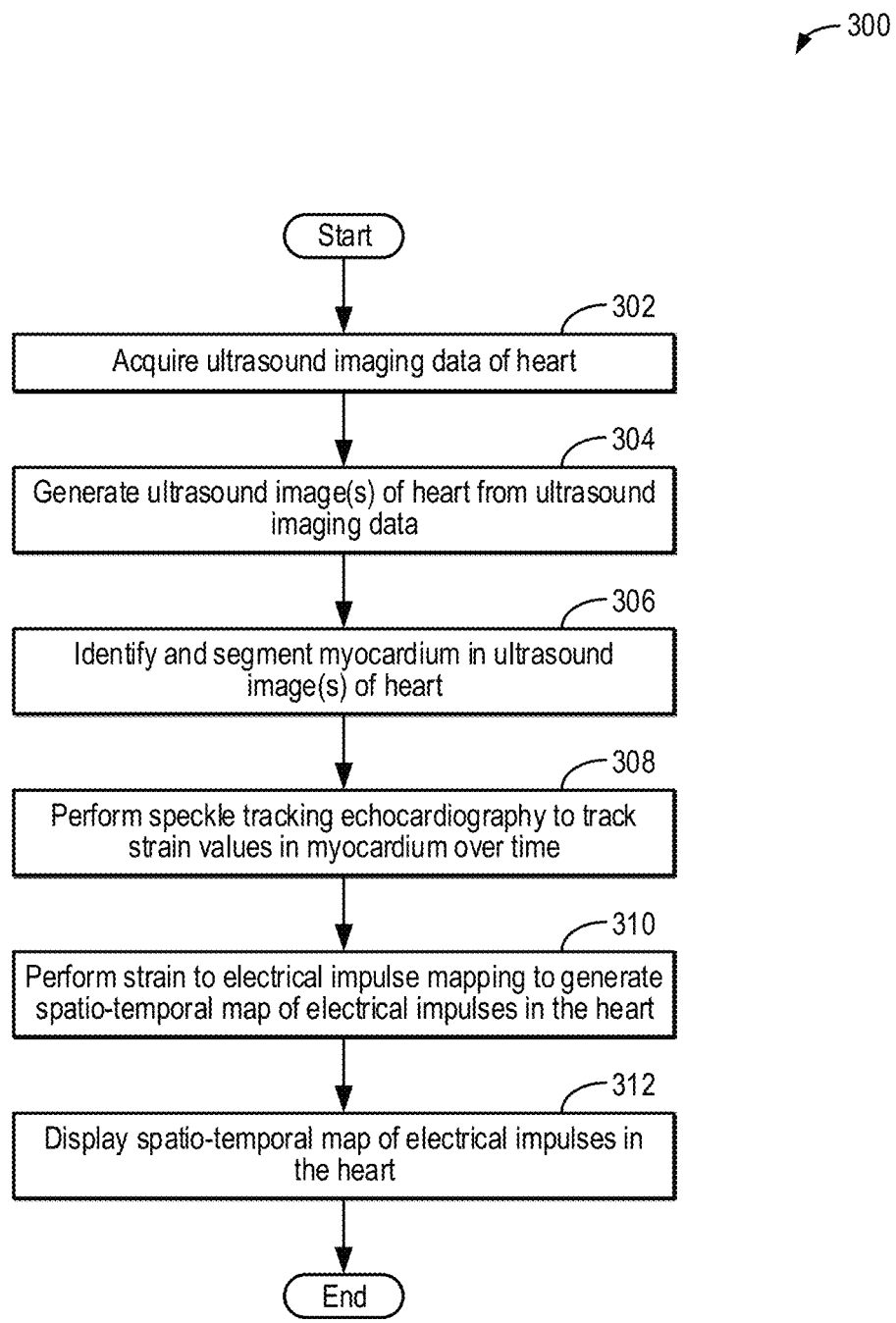
FIG. 3 shows a flow chart of an example method for outputting a cardiac electrical conduction pathway during ultrasound imaging of a heart, according to an embodiment.

FIG. 3 shows an example method 300 for generating a visual depiction of an electrical conduction pathway of a heart of a patient during cardiac ultrasound imaging. The method 300 will be described for ultrasound images acquired using an ultrasound imaging system, such as the ultrasound imaging system 100 of FIG. 1, although other ultrasound imaging systems may be used. Further, the method 300 may be adapted to other imaging modalities. The method 300 may be implemented by one or more of the above described systems, including the ultrasound imaging system 100 of FIG. 1 and the medical image processing system 200 of FIG. 2. As such, the method 300 may be stored as executable instructions in non-transitory memory, such as the memory 120 of FIG. 1 and/or the non-transitory memory 206 of FIG. 2, and executed by a processor, such as the processor 116 of FIG. 1 and/or the processor 204 of FIG. 2. Further, in some embodiments, the method 300 is performed in real-time, as the ultrasound images are acquired, while in other embodiments, at least portions of the method 300 are performed offline, after the ultrasound images are acquired. For example, the processor may evaluate ultrasound images that are stored in memory even while the ultrasound system is not actively being operated to acquire images. Further still, at least parts of the method 300 may be performed in parallel. For example, ultrasound data for a second image may be acquired while a first ultrasound image is generated, ultrasound data for a third image may be acquired while the second ultrasound image is generated, and so on.

At 302, the method 300 includes acquiring ultrasound imaging data of the heart. The ultrasound imaging data may be acquired according to an ultrasound protocol, which may be selected by an operator (e.g., user) of the ultrasound imaging system via a user interface (e.g., the user interface 115). As one example, the operator may select the ultrasound protocol from a plurality of possible ultrasound protocols using a drop-down menu or by selecting a virtual button. Alternatively, the system may automatically select the protocol based on data received from an electronic health record (EHR) associated with the patient. For example, the EHR may include previously performed exams, diagnoses, and current treatments, which may be used to select the ultrasound protocol. Further, in some examples, the operator may manually input and/or update parameters to use for the ultrasound protocol. The ultrasound protocol may be a system guided protocol, where the system guides the operator through the protocol step-by-step, or a user guided protocol, where the operator follows a lab-defined or self-defined protocol without the system enforcing a specific protocol or having prior knowledge of the protocol steps.

Further, the ultrasound protocol may include a plurality of views and/or imaging modes that are sequentially performed. Using cardiac ultrasound imaging as an example, the ultrasound protocol may include a four-chamber view of the left ventricle with B-mode and a four-chamber view focused on the right ventricle with B-mode. It may be understood that in some examples, a partial view of the heart may be acquired, such as a two-chamber view of the left ventricle and left atrium or a single chamber view (e.g., only the left ventricle). In some examples, additional imaging modes may be used, such as color flow imaging (CFI). Further, the ultrasound protocol may specify a frame-rate for acquiring the ultrasound imaging data. The frame-rate for the acquisition may be increased when a regional, partial view of the heart is acquired compared with a full acquisition because a field of view is smaller. The higher frame-rate may result in a more accurate mapping of strain values to electrical activities, as will be elaborated below. However, strain and electrical activities mapping may not be performed on regions outside of the field of view. Therefore, in some examples, a plurality of regional views of the heart may be acquired, with each of the plurality of regional views obtaining a different partial view of the heart, in order to obtain a more accurate mapping of strain and electrical activities in each region.

The ultrasound imaging data may be acquired with an ultrasound probe by transmitting and receiving ultrasonic signals according to the ultrasound protocol. In the above cardiac ultrasound imaging example, performing the ultrasound protocol includes acquiring ultrasound data for some or all of the above-mentioned views and imaging modes. Acquiring the ultrasound data according to the ultrasound protocol may include the system displaying instructions on the user interface and/or display, for example, to guide the operator through the acquisition of the designated views. Additionally or alternatively, the ultrasound protocol may include instructions for the ultrasound system to automatically acquire some or all of the data or perform other functions. For example, the ultrasound protocol may include instructions for the user to move, rotate and/or tilt the ultrasound probe, as well as to automatically initiate and/or terminate a scanning process and/or adjust imaging parameters of the ultrasound probe, such as ultrasound signal transmission parameters, ultrasound signal receive parameters, ultrasound signal processing parameters, or display parameters. Further, the acquired ultrasound data may include one or more image parameters calculated for each pixel or group of pixels (for example, a group of pixels assigned the same parameter value) to be displayed, where the one or more calculated image parameters include, for example, one or more of an intensity, texture, graininess, contractility, deformation, and rate of deformation value.

At 304, the method 300 includes generating ultrasound image(s) of the heart from the acquired ultrasound imaging data. The ultrasound images of the heart may also be referred to herein as cardiac ultrasound images. At least one ultrasound image may be generated for each view of the ultrasound protocol. For example, the signal data acquired during the method at 302 is processed and analyzed by the processor in order to produce an ultrasound image. The processor may include an image processing module that receives the signal data (e.g., image data) acquired at 302 and processes the received image data. For example, the image processing module may process the ultrasound signals to generate slices or frames of ultrasound information (e.g., ultrasound images) for displaying to the operator. In one example, generating the image may include determining an intensity value for each pixel to be displayed based on the received image data (e.g., 2D or 3D ultrasound data). As such, the generated ultrasound images may be 2D or 3D depending on the mode of ultrasound being used (e.g., CFI, acoustic radiation force imaging, B-mode, A-mode, M-mode, spectral Doppler, acoustic streaming, tissue Doppler module, C-scan, or elastography).

At 306, the method 300 includes identifying and segmenting myocardium in the ultrasound image(s) of the heart. For example, each ultrasound image may be input into or more image analysis algorithms in substantially real-time, as each ultrasound image is acquired. Alternatively, each ultrasound image may be processed by the one or more image analysis algorithms offline, after the ultrasound imaging data acquisition is finished. In some embodiments, the one or more image analysis algorithms may be included in a myocardium analysis module, such as the myocardium analysis module 212 described above with respect to FIG. 2. The one or more image analysis algorithms may include image recognition algorithms, shape detection algorithms, and/or edge detection algorithms, for identifying the cardiac muscle. The one or more image analysis algorithms may further include one or more machine learning algorithms and/or traditionally programmed algorithms for identifying and segmenting the myocardium. Further, the myocardium may be divided into a right ventricle portion, a right atrium portion, a left ventricle portion, and a left atrium portion of cardiac muscle surrounding each chamber of the heart. For example, the chambers may be identifiable based on their relative positioning in the ultrasound images and pixel contrast between the brighter (e.g., higher intensity) pixels of the heart tissue and the darker (e.g., lower intensity) pixels of the blood-filled chambers.

At 308, the method 300 includes performing speckle tracking echocardiography to track strain values in the myocardium over time. For example, once identified, the myocardium may be tracked throughout an entire heart cycle to determine how each portion of the myocardium contracts and relaxes through the heart cycle. Each heart cycle comprises one heartbeat, which includes two periods called diastole and systole. During diastole, the myocardium relaxes and the heart refills with blood. During systole, the myocardium contracts to pump the blood out of the heart. The contraction and relaxation cause shortening and elongation of the myocardium, respectfully, which may be quantified via speckle tracking echocardiography.

The speckle tracking echocardiography may include a pre-programmed analysis tool that calculates the strain at a given position of heart muscle as a change in length of the heart muscle at the given position between two time points. Thus, the strain at the given position may change throughout the heart cycle as the muscle expands and contracts. Further, strain values may be determined in a plurality of directions (e.g., longitudinal, circumferential, and radial) that correspond to the change in length in the corresponding direction. For example, a longitudinal strain value may denote a change in length of the heart muscle along its long axis, a circumferential strain value may denote a circumferential change of the associated cavity (e.g., chamber) during the heart cycle, and a radial strain value may denote a change in length of the muscle wall along its radius (e.g., a change in thickness). Each strain value may be given as a percentage change (e.g., negative or positive) between an initial time point (e.g., before an electrical pulse through the heart) and a final time point (e.g., after the electrical pulse through the heart).

As one example, the speckle tracking echocardiography may include defining brighter pixel "speckles" of myocardium that are produced as a result of the scatter of the ultrasound beam by the tissue. The identified speckles may be tracked frame-by-frame to determine a change in their position in different dimensions (e.g., longitudinal, circumferential, and radial). As an illustrative example, the speckle tracking echocardiography may use a sum-of-the absolute-differences algorithm. The speckle tracking echocardiography may further determine a magnitude of myocardial deformation in these different directions over the heart cycle, corresponding to mechanical movement of the heart, to generate the strain values. In some examples, the speckle tracking echocardiography may further generate strain rate curves corresponding to a rate of change in the strain values over time (e.g., over the heart cycle).

At 310, the method 300 includes performing strain to electrical impulse mapping to generate a spatio-temporal map of electrical impulses in the heart. Contraction of the cardiac muscle is initiated by an electrical impulse generated within the heart at the sinoatrial (SA) node, which is positioned in the upper wall of the right atrium. The atrio-ventricular (AV) node, positioned in the wall of the right heart between the atrium and ventricle, is electrically connected to the SA node to coordinate beating of the atria and the ventricles. The electrical impulse travels through the cardiac muscle and causes a train of contraction as it travels in a spatio-temporal fashion. The speckle tracking echocardiography quantifies the contraction pattern at various locations in time, as mentioned above. Because contraction is an immediate effect of passage of electrical impulse, given the strain values, the spatio-temporal map showing the passage of electrical impulses may be generated directly from the strain values. For example, the stronger the electrical impulse, the greater the resulting contraction/expansion (and thus, the greater the measured strain values). Further still, the electrical impulse may not travel through dead heart tissue. As such, a strength (e.g., an intensity) and position of the electrical impulse at a given position the heart at a given time may be directly determined from the strain values at the given position at the given time. That is, portions of the myocardium having the passage of the electrical impulses at a given time point may be identified based on the strain values indicating contraction of those portions of the myocardium at the given time point. Thus, the electrical impulses are mapped to regions of the heart in a space- and time-specific manner in order to synchronize the passage of the electrical impulse with mechanical movement of a particular region, as indicated by the strain values.

As one example, the strength of the electrical impulse at a given position may be determined according to one or more functions stored in the non-transitory memory. For example, the strain values may be input into the one or more functions, which may output the corresponding electrical impulse intensity. For example, the resulting strength may be zero, indicating the electrical impulse is not present, when the strain value indicates that the heart muscle is not contracting at that location. In some embodiments, each strain value may be input into a different function, and the resulting intensity values may be combined (e.g., summed). In other embodiments, the strain values may be combined, and the combined strain value may be input into a single function. Example relationships that relate the strain value(s) to the strength of the electrical impulse are graphically shown in FIG. 5, as will be elaborated below.

At 312, the method 300 includes displaying the spatio-temporal map of the electrical impulses in the heart. As one example, the spatio-temporal map of the electrical impulses in the heart may be generated by overlaying the electrical impulses on the ultrasound images of the heart so that a conduction path of the electrical impulses is synchronized with mechanical movement of the cardiac muscles depicted in the ultrasound images. Additionally or alternatively, the spatio-temporal map of the electrical impulses in the heart may be generated by overlaying the electrical impulses on an animation of the heart in a manner that synchronizes the mechanical movement of the heart with the conduction path of the electrical impulses. For example, the animation of the heart may be generated by adjusting a pre-made heart animation according to the strain values and heart rate observed in the ultrasound images so that the heart animation provides a simplified model of the imaged heart. Displaying the spatio-temporal map of the electrical impulses in the heart may include outputting the spatio-temporal map to one or more display devices, such as the display device 118 of FIG. 1. Further, a pixel brightness of the electrical impulses may directly correlate to the intensity of the electrical impulse at that location, such as determined above, so that the user or another clinician may easily observe areas of weak conduction. The method 300 may then end.

It may be appreciated that in alternative embodiments, a neural network may be used in place of performing the speckle tracking echocardiography. In such embodiments, the ultrasound images generated from the ultrasound imaging data may be directly input into a neural network, and the neural network may output the spatio-temporal map of the electrical impulses in the heart without performing the speckle tracking echocardiography and strain to electrical impulse mapping. The neural network may be trained with previously acquired cardiac ultrasound images and associated spatio-temporal maps of electrical impulses in the heart generated via speckle tracking echocardiography, such as according to the method 300 described above.

Turning now to FIG. 4, an example segmented cardiac ultrasound image 400 is shown. The segmented cardiac ultrasound image 400 is a B-mode grayscale image and shows a four-chamber view of a heart 402. The heart 402 is segmented into a right atrium 404, a right ventricle 406, a left atrium 408, and a left ventricle 410. Further, brighter pixel speckles 412 are visible in the segmented cardiac ultrasound image 400, which may be used for speckle tracking echocardiography, such as described above with respect to FIG. 4. For example, tracking the displacement of speckles 412 between image frames in the right ventricle 406 may provide strain values that are specific for the right ventricle, whereas tracking speckles 412 in the left atrium 408 may provide different strain values that are specific for the left atrium.

Segmenting the myocardium may enable a speckle tracking algorithm to distinguish between contractile heart tissue (e.g., the myocardium) and non-contractile heart tissue (e.g., the pericardium) determine strain values specifically for the contractile tissue. Because the pericardium does not contract, including the pericardium in a strain calculation may result in both regional and global strain values being underestimated. Further, electrical impulses do not travel through non-contractile tissue. Thus, an accuracy of the strain calculation and the resulting electrical impulse mapping may be increased by segmenting the myocardium before performing the speckle tracking echocardiography.

Next, FIG. 5 shows a graph 500 of example relationships between a magnitude of a strain value (horizontal axis) and an electrical impulse intensity (vertical axis). A first plot 502 shows a first relationship between the strain value and the electrical impulse intensity, a second plot 504 shows a second relationship between the strain value and the electrical impulse intensity, and a third plot 506 shows a third relationship between the strain value and the electrical impulse intensity. As can be seen by each of the first plot 502, the second plot 504, and the third plot 506, in general, the electrical impulse intensity increases as the strain value increases. However, the relationship may be linear (e.g., second plot 504) or non-linear (e.g., first plot 502 and third plot 506). In some examples, the first plot 502, the second plot 504, and the third plot 506 describe relationships between the strain value and the electrical impulse intensity for different types of strain. For example, the first plot 502 may correspond to circumferential strain, the second plot 504 may correspond to longitudinal strain, and the third plot 506 may correspond to radial strain. In some examples, the example relationships may be adjusted based on, for example, a rate of change in the strain values over time. For example, a slope of the first plot 502, the second plot 504, and/or the third plot 506 may be adjusted based on the rate of change in the strain values. In still other examples, more or fewer than three relationships may be used in mapping the strain values to electrical impulse intensity. Further, in some examples, instead of electrical impulse intensity, the strain value may be directly correlated to the pixel intensity to display for the spatio-temporal map of the electrical impulses through the heart.

As shown in each of the first plot 502, the second plot 504, and the third plot 506, the electrical impulse intensity is zero when the strain value is zero. That is, if a portion of heart muscle is dead (e.g., no contraction occurs), the strain value is zero, and the corresponding electrical impulse intensity is also zero. If the strain value is high, the electrical impulse travels quickly through that muscle. In contrast, if the strain value is low, the electrical impulse travels more slowly through that muscle. Thus, the strain value and the electrical impulse are positively correlated. Further, it may be understood that the electrical impulse is a closed circuit in one direction and does not travel backwards.

FIG. 6 shows an example sequence 600 of display outputs that may occur while acquiring cardiac ultrasound images and generating a spatio-temporal map of an electrical conduction pathway through the heart. The sequence 600 shows a series of image frames with respect to a time axis 620, including first image frame 601, a second image frame 603, a third image frame 605, a fourth image frame 607, a fifth image frame 609, and a sixth image frame 611. Together, the first through sixth image frames depict one heart cycle. The first image frame 601 is the earliest frame, and the sixth image frame 611 is the latest time frame, as shown by the time axis 620. It may be understood that additional image frames may exist between consecutive image frames in the sequence 600, and the spacing between each consecutive image frame is meant to denote a relative arrangement of each image frame with respect to time and not a particular duration of time between each image frame. Each image frame depicts a single snapshot in time of an animation of electrical impulses in a heart 602. A two-dimensional, cross-sectional view of the heart 602 is shown in FIG. 6. However, in other examples, a three-dimensional representation of the heart 602 may be depicted. In particular, the cross-sectional view enables a right atrium 604, a right ventricle 606, a left atrium 608, a left ventricle 610, a SA node 612, and an AV node 614 to be easily viewed in each image frame.

An electrical impulse 616 is initiated at the SA node 612 and travels via an interatrial pathway to the left atrium 608 in the first image frame 601, causing both the right atrium 604 and the left atrium 608 to contract and associated valves to open. The first image frame 601 is output to a display (e.g., display device 118 of FIG. 1) at a first time point t1. For example, the first image frame 601 may be output to the display in substantially real-time, as the cardiac ultrasound image is acquired. Shaded regions 618 indicate regions of the display that may have a greater pixel brightness in order to denote the intensity of the electrical impulse 616 at those regions of the heart 602. The electrical impulse 616 travels to the AV node 614 via an intermodal pathway and is no longer traveling to the left atrium 608 in the second image frame 603. As a result, the left atrium 608 relaxes in the second image frame 603. The second image frame 603 is output to the display at a second time point t2.

From the AV node 614, the electrical impulse 616 travels down bundle branches in the third image frame 605, which is output to the display at a third time point t3, and the fourth image frame 607, which is output to the display at a fourth time point t4. The electrical impulse 616 continues to Purkinje fibers located in the inner walls of the right ventricle 606 and the left ventricle 610 in the fifth image frame 609, which causes the right ventricle 606 and the left ventricle 610 to both contract. The fifth image frame 609, which visually indicates the electrical impulse 616 causing the contraction of the right ventricle 606 and the left ventricle 610, is output to the display at a fifth time point t5. The electrical impulse 616 terminates at the Purkinje fibers, allowing the heart (particularly the right ventricle 606 and the left ventricle 610) to relax. This is visually indicated in the sixth image frame 611, which depicts the absence of the electrical impulse 616 and the expanded ventricles. The sixth image frame 611 is output to the display at a sixth time point t6. The sequence 600 may repeat for additional heart cycles. Thus, the sequence 600 maps a position of the electrical impulse 616 at a given time point in the heart cycle to areas undergoing myocardial deformation at the given time point.

In this way, a spatio-temporal map of an electrical conduction pathway through the heart may be generated and displayed to a user. The spatio-temporal map of the electrical conduction pathway may be more easily interpreted than a strain value map, for example. For example, the spatio-temporal map of the electrical conduction pathway may combine strain values reported in different directions into a single dynamic visual. As a result, areas of weak heart muscle or dead tissue may be more easily identified. By more easily identifying areas of weak heart muscle or dead tissue, a time to diagnosis may be decreased, enabling faster patient interventions for more positive patient outcomes.

A technical effect of using strain values determined from cardiac ultrasound images to map electrical impulses through the heart is that a relationship between electrical and mechanical activity in the heart may be accurately visualized.

The disclosure also provides support for a method, comprising: generating cardiac ultrasound images from ultrasound imaging data of a heart, generating a spatio-temporal map of electrical impulses in the heart based on contraction and elongation of cardiac muscles depicted in the cardiac ultrasound images, and outputting the spatio-temporal map of the electrical impulses in the heart to a display device. In a first example of the method, generating the spatio-temporal map of the electrical impulses in the heart based on the contraction and the elongation of the cardiac muscles depicted in the cardiac ultrasound images comprises: identifying and segmenting the cardiac muscles, determining strain values in the identified and segmented cardiac muscles via speckle tracking echocardiography, and determining a strength and a position of the electrical impulses at each portion of the identified and segmented cardiac muscles based on the strain values at a given portion. In a second example of the method, optionally including the first example, the strength of the electrical impulses at the given portion increases as a magnitude of the strain values increases, and wherein the strength of the electrical impulses corresponds to a brightness of a pixel of the display device. In a third example of the method, optionally including one or both of the first and second examples, determining the strain values comprises determining a change in a length of the given portion of the identified and segmented cardiac muscles between an initial time point and a final time point. In a fourth example of the method, optionally including one or more or each of the first through third examples, the strain values comprise a longitudinal strain value, a circumferential strain value, and a radial strain value. In a fifth example of the method, optionally including one or more or each of the first through fourth examples, generating the spatio-temporal map of the electrical impulses in the heart based on the contraction and the elongation of the cardiac muscles comprises: inputting the cardiac ultrasound images generated from the ultrasound imaging data into a neural network, and receiving the spatio-temporal map of the electrical impulses in the heart as an output of the neural network. In a sixth example of the method, optionally including one or more or each of the first through fifth examples, the neural network is trained using previously acquired cardiac ultrasound images and associated electrical conduction pathways generated via speckle tracking echocardiography. In a seventh example of the method, optionally including one or more or each of the first through sixth examples, outputting the spatio-temporal map of the electrical impulses in the heart to the display device comprises overlaying the electrical impulses in the heart on the cardiac ultrasound images, wherein a position of the electrical impulses is synchronized with mechanical movement of the cardiac muscles depicted in the cardiac ultrasound images. In an eighth example of the method, optionally including one or more or each of the first through seventh examples, outputting the spatio-temporal map of the electrical impulses in the heart to the display device comprises: generating an animation of the heart, and overlaying the electrical impulses in the heart on the animation of the heart, wherein a position of the electrical impulses is synchronized with mechanical movement of the heart at a given time point of the animation.

The disclosure also provides support for a method, comprising: acquiring ultrasound imaging data of a heart, identifying myocardium in images generated from the ultrasound imaging data, determining strain values at each portion of the myocardium in the images, and outputting an electrical conduction pathway through the heart that is generated based on the determined strain values. In a first example of the method, identifying the myocardium in the images generated from the ultrasound imaging data comprises analyzing the images via at least one of an image recognition algorithm, a shape detection algorithm, and an edge detection algorithm. In a second example of the method, optionally including the first example, determining strain values at each portion of the myocardium in the images comprises performing speckle tracking echocardiography on the images. In a third example of the method, optionally including one or both of the first and second examples, the strain values comprise a longitudinal strain value corresponding to a length change in a given portion of the myocardium during a heart cycle, circumferential strain value corresponding to a circumference change of an associated chamber of the given portion of the myocardium during the heart cycle, and a radial strain value corresponding to a change in thickness of the given portion of the myocardium along its radius. In a fourth example of the method, optionally including one or more or each of the first through third examples, outputting the electrical conduction pathway through the heart that is generated based on the determined strain values comprises: mapping a passage of electrical impulses through the heart to the strain values in a spatio-temporal fashion. In a fifth example of the method, optionally including one or more or each of the first through fourth examples, mapping the passage of the electrical impulses through the heart to the strain values in the spatio-temporal fashion: identifying portions of the myocardium having the passage of the electrical impulses at a given time point based on the strain values indicating contraction of the portions of the myocardium at the given time point.

The disclosure also provides support for a system, comprising: an ultrasound probe, a display device, and a processor configured to execute instructions stored in non-transitory memory that, when executed, cause the processor to: acquire ultrasound imaging data of a heart via the ultrasound probe, generate cardiac ultrasound images from the acquired ultrasound imaging data of the heart, determine an electrical conduction pathway during a heart cycle of the heart based on myocardial deformation in the heart during the heart cycle, and output an animation of the electrical conduction pathway on the display device. In a first example of the system, to determine the electrical conduction pathway during the heart cycle of the heart based on the myocardial deformation in the heart during the heart cycle, the processor is configured to execute further instructions stored in the non-transitory memory that, when executed, cause the processor to: perform speckle tracking echocardiography on the generated cardiac ultrasound images to calculate strain values that quantify the myocardial deformation in the heart during the heart cycle, and map a position of electrical impulses at a given time point in the heart cycle to areas undergoing the myocardial deformation at the given time point. In a second example of the system, optionally including the first example, the animation of the electrical conduction pathway comprises an overlay of the electrical conduction pathway on the cardiac ultrasound images, and wherein a pixel brightness of the electrical conduction pathway increases as a magnitude of the myocardial deformation in the heart increases. In a third example of the system, optionally including one or both of the first and second examples, to determine the electrical conduction pathway during the heart cycle of the heart based on the myocardial deformation in the heart during the heart cycle, the processor is configured to execute further instructions stored in the non-transitory memory that, when executed, cause the processor to: input the generated cardiac ultrasound images into a neural network, and receive the animation of the electrical conduction pathway as an output of the neural network. In a fourth example of the system, optionally including one or more or each of the first through third examples, the neural network is trained using previously acquired cardiac ultrasound images and associated electrical conduction pathways generated by mapping strain values to positions of electrical impulses in the heart in a space- and time-specific manner.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   generating cardiac ultrasound images from ultrasound imaging data of a heart;
   determining strain values at each portion of myocardium in the cardiac ultrasound images, wherein strain values are determined by contraction and elongation of the myocardium depicted in the cardiac ultrasound images;
   generating a spatio-temporal map of electrical impulses in the heart from the strain values; and
   outputting the spatio-temporal map of the electrical impulses in the heart to a display device, wherein the spatio-temporal map represents an electrical conduction pathway through the heart that is generated from the strain values;
   wherein the spatio-temporal map is an animation of the heart made by adjusting a pre-made heart animation according to the strain values and a heart rate observed in the ultrasound imaging data of the heart.

2. The method of claim 1, wherein generating the spatio-temporal map of the electrical impulses in the heart from the strain values comprises:
   determining the strain values in the identified and segmented cardiac muscles via speckle tracking echocardiography; and
   determining a strength and a position of the electrical impulses at each portion of the identified and segmented cardiac muscles based on the strain values at a given portion.

3. The method of claim 2, wherein the strength of the electrical impulses at the given portion increases as a magnitude of the strain values increases, and wherein the strength of the electrical impulses corresponds to a brightness of a pixel of the display device.

4. The method of claim 2, wherein determining the strain values comprises determining a change in a length of the given portion of the identified and segmented cardiac muscles between an initial time point and a final time point.

5. The method of claim 2, wherein the strain values comprise a longitudinal strain value, a circumferential strain value, and a radial strain value.

6. The method of claim 1, wherein generating the spatio-temporal map of the electrical impulses in the heart from the strain values comprises:
inputting the cardiac ultrasound images generated from the ultrasound imaging data into a neural network; and
receiving the spatio-temporal map of the electrical impulses in the heart as an output of the neural network.

7. The method of claim 6, wherein the neural network is trained using previously acquired cardiac ultrasound images and associated electrical conduction pathways generated via speckle tracking echocardiography.

8. The method of claim 1, wherein outputting the spatio-temporal map of the electrical impulses in the heart to the display device comprises overlaying the electrical impulses in the heart on the cardiac ultrasound images, wherein a position of the electrical impulses is synchronized with mechanical movement of cardiac muscles depicted in the cardiac ultrasound images.

9. The method of claim 1, wherein outputting the spatio-temporal map of the electrical impulses in the heart to the display device comprises:
generating an animation of the heart; and
overlaying the electrical impulses in the heart on the animation of the heart, wherein a position of the electrical impulses is synchronized with mechanical movement of the heart at a given time point of the animation.

10. A method, comprising:
acquiring ultrasound imaging data of a heart;
identifying myocardium in images generated from the ultrasound imaging data;
determining strain values at each portion of the myocardium in the images, wherein the strain values are based on contraction and elongation of cardiac muscles depicted in the images;
generating a spatio-temporal map of electrical impulses in the heart from the determined strain values; and
outputting the spatio-temporal map of the electrical impulses in the heart to a display device, wherein the spatio-temporal map represents an electrical conduction pathway through the heart that is generated from the determined strain values;
wherein generating the spatio-temporal map comprises overlaying the electrical impulses on a simplified heart model and synchronizing the electrical impulses with the contraction and the elongation of the cardiac muscles.

11. The method of claim 10, wherein identifying the myocardium in the images generated from the ultrasound imaging data comprises analyzing the images via at least one of an image recognition algorithm, a shape detection algorithm, and an edge detection algorithm.

12. The method of claim 10, wherein determining strain values at each portion of the myocardium in the images comprises performing speckle tracking echocardiography on the images or inputting the images into a neural network and receiving the electrical conduction pathway as an output of the neural network.

13. The method of claim 10, wherein the strain values comprise a longitudinal strain value corresponding to a length change in a given portion of the myocardium during a heart cycle, circumferential strain value corresponding to a circumference change of an associated chamber of the given portion of the myocardium during the heart cycle, and a radial strain value corresponding to a change in thickness of the given portion of the myocardium along its radius.

14. The method of claim 10, wherein outputting the spatio-temporal map of the electrical impulses comprises:
mapping a passage of the electrical impulses through the heart to the strain values in a spatio-temporal fashion.

15. The method of claim 14, wherein mapping the passage of the electrical impulses through the heart to the strain values in the spatio-temporal fashion comprises:
identifying portions of the myocardium having the passage of the electrical impulses at a given time point based on the strain values indicating contraction of the portions of the myocardium at the given time point.

16. A system, comprising:
an ultrasound probe;
a display device; and
a processor configured to execute instructions stored in non-transitory memory that, when executed, cause the processor to:
acquire ultrasound imaging data of a heart via the ultrasound probe;
generate cardiac ultrasound images from the acquired ultrasound imaging data of the heart;
determine strain values at each portion of myocardium in the cardiac ultrasound images, wherein strain values are determined by contraction and elongation of the myocardium depicted in the cardiac ultrasound images;
generate a spatio-temporal map of electrical impulses in the heart from the strain values; and
output the spatio-temporal map of the electrical impulses in the heart to the display device, wherein the spatio-temporal map represents an electrical conduction pathway through the heart that is generated from the strain values;
wherein the electrical conduction pathway is overlaid on a heart animation, wherein the heart animation is a simplified model that is adjusted according to the strain values and an observed heart rate of the acquired ultrasound imaging data.

17. The system of claim 16, wherein to generate the spatio-temporal map, the processor is configured to execute further instructions stored in the non-transitory memory that, when executed, cause the processor to:
perform speckle tracking echocardiography on the generated cardiac ultrasound images to calculate the strain values that quantify myocardial deformation in the heart during a heart cycle; and
map a position of the electrical impulses at a given time point in the heart cycle to areas undergoing the myocardial deformation at the given time point.

18. The system of claim 16, wherein the spatio-temporal map comprises an overlay of the electrical conduction pathway on the cardiac ultrasound images, and wherein a pixel brightness of the electrical conduction pathway increases as a magnitude of deformation of the myocardium increases.

19. The system of claim 16, wherein to determine the electrical conduction pathway during a heart cycle of the heart based on a myocardial deformation in the heart during the heart cycle, the processor is configured to execute further instructions stored in the non-transitory memory that, when executed, cause the processor to:

input the generated cardiac ultrasound images into a neural network; and receive the spatio-temporal map of the electrical conduction pathway as an output of the neural network.

20. The system of claim 19, wherein the neural network is trained using previously acquired cardiac ultrasound images and associated electrical conduction pathways generated by mapping strain values to positions of electrical impulses in the heart in a space-and time-specific manner.

* * * * *